United States Patent
Brenker et al.

(10) Patent No.: US 10,267,724 B2
(45) Date of Patent: Apr. 23, 2019

(54) DEVICE AND METHOD FOR THE OPTICAL STIMULATION OF AN OPTICALLY ACTIVATABLE BIOLOGICAL SAMPLE

(71) Applicant: ALBERT-LUDWIGS-UNIVERSITÄT FREIBURG, Freiburg (DE)

(72) Inventors: Kathrin Brenker, Freiburg (DE); Jianying Yang, Freiburg (DE); Michael Reth, Freiburg (DE)

(73) Assignee: Albert-Ludwigs-Universität Freiburg, Freiburg (DE)

( * ) Notice: Subject to any disclaimer, the term of this patent is extended or adjusted under 35 U.S.C. 154(b) by 0 days.

(21) Appl. No.: 15/757,650

(22) PCT Filed: Aug. 29, 2016

(86) PCT No.: PCT/EP2016/070277
§ 371 (c)(1),
(2) Date: Mar. 5, 2018

(87) PCT Pub. No.: WO2017/036999
PCT Pub. Date: Mar. 9, 2017

(65) Prior Publication Data
US 2019/0025187 A1 Jan. 24, 2019

(30) Foreign Application Priority Data
Sep. 3, 2015 (DE) .......................... 10 2015 216 841

(51) Int. Cl.
*G01N 21/69* (2006.01)
*G01N 15/14* (2006.01)
(Continued)

(52) U.S. Cl.
CPC ..... *G01N 15/1459* (2013.01); *G01N 15/1434* (2013.01); *G01N 15/1436* (2013.01);
(Continued)

(58) Field of Classification Search
CPC .......... G01N 15/1459; G01N 15/1436; G01N 2015/1006; G01N 2015/1081; G01N 15/1484; G01N 15/1434; G01N 21/6452
See application file for complete search history.

(56) References Cited

U.S. PATENT DOCUMENTS

| 3,734,845 A | 5/1973 | Jean-Claude Bravi et al. |
| 5,637,469 A * | 6/1997 | Wilding .............. B01F 15/0264 366/DIG. 3 |

(Continued)

FOREIGN PATENT DOCUMENTS

| WO | 9509814 A1 | 4/1995 |
| WO | 9942809 A1 | 8/1999 |
| WO | 2005017498 A1 | 2/2005 |

OTHER PUBLICATIONS

International Search Report issued against corresponding international application No. PCT/EP2016/070277.

*Primary Examiner* — Kiho Kim
(74) *Attorney, Agent, or Firm* — Fitch, Even, Tabin & Flannery LLP

(57) ABSTRACT

The invention relates to a device (1) and a method for the optical stimulation of an optically activatable biological sample (3), comprising at least one light source (13; 13', 13"), which emits light of at least one predetermined wavelength that impinges directly or indirectly on the sample (3). The invention is characterized in that: the at least one light source (13; 13', 13") is thermally coupled to a hollow channel section (4); the hollow channel section (4) is part of a fluid circuit through which fluid flows; a temperature-control unit (12) and a conveying pump are arranged along the fluid circuit; and the hollow channel section (4) has at least one limiting wall (5) onto which the optically activatable biological samples (3) are thermally coupled in a direct or indirect manner.

28 Claims, 4 Drawing Sheets

(51) Int. Cl.
*G01N 21/64* (2006.01)
*G01N 15/10* (2006.01)

(52) U.S. Cl.
CPC ..... *G01N 15/1484* (2013.01); *G01N 21/6452* (2013.01); *G01N 2015/1006* (2013.01); *G01N 2015/1081* (2013.01)

(56) References Cited

U.S. PATENT DOCUMENTS

| | | |
|---|---|---|
| 2005/0030519 A1 | 2/2005 | Roth |
| 2005/0225745 A1 | 10/2005 | Nagai |
| 2014/0084179 A1 | 3/2014 | Ben-Hur et al. |
| 2015/0107993 A1* | 4/2015 | Izquierdo ............... C12Q 1/02 204/403.01 |

* cited by examiner

DEVICE AND METHOD FOR THE OPTICAL STIMULATION OF AN OPTICALLY ACTIVATABLE BIOLOGICAL SAMPLE

CROSS REFERENCE TO RELATED APPLICATIONS

Reference is made to International Application No. PCT/EP2016/070277, filed Aug. 29, 2016, and German Application No. 10 2015 216 841.7, filed Mar. 9, 2015, which are incorporated herein by reference in their entirety.

BACKGROUND OF THE INVENTION

Field of the Invention

The invention relates to a device and a method for the optical stimulation of an optically activatable biological sample with at least one light source, which emits light of at least one selectable wavelength, which impinges directly or indirectly on the sample.

Description of the Prior Art

For both the quantitative measurement and the molecular characterization of biological cells, so-called flow cytometers are used, which comprise a flow measuring cell, usually in the form of a light-transparent micro-channel cuvette, through which isolated cells from a pre-stored cell suspension flow sequentially. Along the micro-channel cuvette an arrangement of light sources is arranged, usually in the form of one or more lasers, the light beam of which laterally irradiates or permeates each individual cell when passing through a defined measuring region along the micro-channel cuvette. Using suitably arranged photodetectors, both scattering components of the stimulating laser light and fluorescent light phenomena excited by the laser radiation, which usually originate from fluorescent markers adhering to the cells or cell components, can be detected, which are used for the simultaneous analysis of physical and molecular properties of the individual cells.

Document WO 2005/017498 A1 discloses a generic flow cytometer, which instead of the above-mentioned lasers uses light emitting diodes, or LEDs for short, as the light source. The LEDs irradiate the individual cells under different angles of incidence and/or with different wavelengths. In an appropriate way, a plurality of detectors is used for detecting the scattered light components and the fluorescent light, which is emitted due to fluorescence by the cell, or fluorescent markers adhering to the cells. Since only very few biological cells can be optically excited to fluorescence themselves, fluorescent dyes are bound to certain constituents of the cell. To "colour" the cells, fluorescent dye-marked antibodies are used, which selectively bind to specific surface proteins of the cell. In addition, other coupling mechanisms are known, via which fluorescent markers are deposited intracellularly on certain cell components or intracellular ions.

If dyes having different fluorescence properties are also used, the fluorescent excitation of which requires specific excitation wavelengths, by the use of differently coloured light sources, and by providing appropriate filters within a flow cytometer, the number of cell characteristics that can be distinguished and therefore the information density that is detectable by means of the flow cytometer, can be significantly increased.

Typical applications of flow cytometers are the analysis of the DNA content of tumour cells, for example, or the determination of the concentration of cells, which are identifiable via suitably coloured antibodies as mentioned above. Beyond the mere phenotyping of individual cells, the detection of fluorescent light signals can also be used for the functional characterization of cells. An important method suitable accomplishing this task is, for example, the analysis of biochemical signals or signalling paths, such as ion concentrations or enzyme reactions in response to an optical stimulation of cells. In such studies, it is essential that signal changes which can be initiated by the optical stimulation event, are detected by measurement techniques as far as possible without time delays, preferably, instantaneously. In other words, it is desirable that between the manipulation of the biochemical signal or signal pathway and the measurement of the effect, as little time elapses as possible.

A known flow cytometer is disclosed in document US 2005/0225745, in which a first light source is directed onto the liquid sample to be analysed in order to generate both forward-scattered and laterally-scattered light at the sample. A second light source is capable of generating fluorescent light in interaction with the sample. A first detector detects the forward-scattered light, a second detector detects the laterally scattered light, and a third detector detects the fluorescent light.

Document WO 99/42809 describes an arrangement for cell analysis by the method of optical stimulation. A liquid that contains cells to be analysed flows through a light-transparent channel, to the channel wall of which at least one modified wall region is provided, to which cells adhere. It is just this wall region that is illuminated, and the light passing through the wall region and the cells is detected and analysed. The light sources can be selected arbitrarily and have no further contact with the rest of the measuring arrangement.

SUMMARY OF THE INVENTION

The invention is a device and a method for the optical stimulation of an optically activatable biological sample, in such a way that reproducible conditions for the optical stimulation of the sample are created in a controlled manner, under which stimulation-induced changes in the biochemical or biological signals or signal pathways are formed in the sample. A further object is to create the facility whereby the sensor-based detection of the stimulation-induced changes in the biochemical and/or biological signals and/or signalling pathways is possible by means of a flow cytometer meter in situ, or at least within a defined time period after the optical stimulation, that is to say, within seconds to minutes.

The device according to the invention for the optical stimulation of an optically activatable biological sample with at least one light source, which emits light of at least one selectable wavelength, which impinges directly or indirectly on the sample, is characterized in accordance with the solution by the fact that the at least one light source is thermally coupled to a hollow channel section, which forms part of a fluid circuit through which fluid is flowing, along which a temperature control unit and a conveying pump are arranged. At the same time, the hollow channel section has at least one bounding wall, onto which the optically-activatable biological sample is thermally coupled in a direct or indirect manner.

The term "optical stimulation" is essentially understood to mean an interaction of an optically activatable, biological sample with light. Optical stimulation also includes the meaning of the following terms: optical activation, optical regulation.

The term "optically activatable, biological sample" is understood to mean biological cells or cell constituents, which either inherently or as a result of biochemical restructuring, for instance due to deposition of at least one optically activatable substance onto the sample, are enabled to interact with light.

In a departure from previous practice for optical stimulation of an optically activatable biological sample, in which the sample is usually stored in a cuvette arrangement and optically stimulated by means of manual irradiation, wherein at least the irradiation intensity is not subject to any defined regulation and, moreover, the sample temperature and measuring temperature depend on the prevailing ambient temperature, the device according to the solution creates, by the thermal coupling of both the at least one light source and the optically activatable sample to a temperature-controlled fluid circuit through which fluid flows, physically defined measurement conditions, which are a prerequisite for scientifically reliable, i.e. reproducible measurement signals, which are obtained by means of a flow cytometer.

The device according to the invention ensures on the one hand the operation of the at least one light source at constant temperature. In this way, temperature-induced fluctuations or variations can be avoided in both the emitted light intensity and the wavelength of the light. In this way, the at least one light source can be operated in a thermally frequency-stabilized manner. Furthermore, a temperature-dependent influence on the biochemical and/or biological signal changes generated by optical stimulation can be eliminated. Temperature dependencies of this kind would adversely impact in particular on further analysis of the detected measurement signals in relation to cell-physiological parameters, such as pH, calcium, membrane potential, etc.

In a preferred embodiment, for the purposes of thermal coupling to the temperature-controlled fluid circuit which is permeated by fluid, the at least one light source is designed and arranged such that at least part of the at least one light source is arranged inside the fluid channel section. Naturally, this assumes that at least in some regions, the light source is encapsulated in a fluid-tight manner against the fluid circuit, to prevent any impairment of the operation of the light source. In an advantageous manner, the at least one light source is implemented as a light-emitting diode, or LED for short, or in the form of a laser-based light source. Naturally, it is also possible in principle to use other light sources, such as mercury, xenon or argon lamps.

A preferred exemplary embodiment of the device according to the solution provides a hollow channel section designed as a hollow cylinder, through which fluid flows and the inner and outer peripheral surface of which radially bound a flow volume for the fluid circuit. The inner peripheral surface of the hollow cylindrical hollow channel section represents the at least one bounding wall, via which the optically activatable biological sample is thermally coupled onto the fluid circuit. The thermal coupling can in principle be implemented in two ways.

Firstly, let us assume that the optically activatable biological sample, present in the form of a suspension, is stored in a sample container which is designed in the form of an optically transparent, cuvette-like vessel. The bounding wall of the hollow channel section is designed as part of a receiving structure, into which the cuvette-like sample container can be inserted, wherein the bounding wall of the hollow channel container completely encloses the sample container in the circumferential direction thereof, so as to ensure that the thermal coupling is produced homogeneously in the circumferential direction of the sample container, so as to guarantee a maximally isotropic temperature distribution within the suspension containing the biological sample.

The receiving structure and the sample container are geometrically matched to each other in such a way that, in the inserted condition inside the receiving structure, the sample container directly or indirectly touches the bounding wall and is completely thermally coupled thereto. As can be ascertained from the remainder of the description in conjunction with the illustrated exemplary embodiment, the preferably straight-cylindrically designed bounding wall of the hollow channel section comprises a cup-shaped receiving volume, which is bounded by a base plate and is designed open facing the base plate in the axial direction. The size and shape of the cup-shaped receiving volume is matched to the outer contour of the cuvette-shaped sample container, so that the cuvette wall immediately adjoins the bounding wall of the hollow channel and is thus ideally thermally coupled thereto.

A second implementation option dispenses with a separate sample container for supplying the suspension-based sample. Instead, the suspension is poured directly into the cup-shaped receiving volume, as explained above, so that the bounding wall of the hollow channel section both separates the suspension-based sample and the temperature-controlled fluid and also directly thermally couples them to each other.

The at least one light source is arranged relative to the hollow cylinder-like hollow channel section in such a way that the emission aperture associated with each light source is directed radial inwards, so that the major proportion of the light emitted by the light source is directed onto the bounding wall and thus onto the sample, present in the form of a suspension, arranged radially inside the boundary wall.

The fluid flowing inside the fluid circuit is optically transparent, so that the light path passing through the fluid causes no light losses, or as little as possible. Thus a preferred design and arrangement of the at least one light source provides a light source body which fluid at least partially flows around, and which partly protrudes into the hollow channel section and is directly immersed in the flow of the temperature-controlled fluid. The light emitted by the light source thus firstly penetrates an optically transparent fluid-tight encapsulation against the fluid, the fluid itself, and at least the bounding wall, behind which the biological sample is present in suspension. Preferably, a plurality of light sources is arranged in a distribution which is oriented both in the axial direction and in the circumferential direction of the hollow channel section, so that the biological sample is also irradiated with light as evenly as possible in the circumferential direction.

Preferably, the plurality of the light sources can be divided into at least two groups, wherein the at least two groups of light sources differ from each other in one of the following properties:

beam intensity, emitted wavelength or wavelength spectrum. In this way, the sample can be individually optically stimulated or activated in a controlled manner, both in terms of irradiation time, irradiation intensity and also irradiation spectrum.

For the purposes of the controlled irradiation, the invention provides a control and/or regulating device, which controls or regulates the temperature controlled unit, the fluid pump and/or the at least one light source. The control or regulation is carried out according to a temporally defined selectable irradiation time of the sample with light at a constant selectable light intensity and wavelength or with a specifiable wavelength spectrum and a defined temperature within the fluid circuit through which fluid flows. Of course, different control or regulation methods are conceivable, for instance, variably defined selectable light intensities, wavelengths or wavelength spectra. Other examination patterns can also be of interest, in which the temperature level of the sample and/or the activation of the light sources are varied while being matched to each other.

The device according to the invention described above for optical stimulation of an optically activatable biological sample enables a defined optical conditioning and/or optical stimulation of the sample, the biochemical or bioelectrical properties of which can be selectively manipulated, directly followed by a detection of the sample with a flow cytometer with no time delay. The device according to the solution allows such opto-genetically induced manipulations to be analysed in real time with a flow cytometer. To achieve this, the capillary measuring tube of the flow cytometer protrudes directly into the receiving volume of the device and/or sample vessel, so that a cell uptake by the flow cytometer for analysis purposes is possible at any time, in other words, before, during and/or after the optical stimulation of the optically activatable biological sample located in the receiving volume. For this purpose, the receiving volume is designed open at the top, so that the measuring capillary of the flow cytometer protrudes directly into the receiving volume of the device or sample container. Of course, alternative fluid connections between the receiving volume and the flow cytometer are conceivable, for example, by means of a suitably designed fluid conduit.

For the purposes of a maximally automatic process of both the optical stimulation of the biological sample and of the measurement using the flow cytometer, the control and/or regulation device can transfer signals by wired or wireless means to and from a control device of the flow cytometer, so that, coordinated with the optical stimulation, a pump-based extraction by the flow cytometer of at least a portion of the sample takes place from the receiving volume into the measuring capillary of the flow cytometer, and a cytometric analysis of the sample is subsequently performed.

The device according to the invention is based on the method that, before or during the execution of a cytometric analysis, the sample is irradiated with a controlled, selectable light intensity and wavelength and/or a selectable wavelength spectrum, wherein the light is emitted from at least one light source, which is temperature-controlled by a temperature-controlled fluid, to which the sample itself is thermally coupled at the same time. The sample itself is preferably temperature controlled, that is to say, preferably held at a constant temperature, for example 37° C., before, during and/or after the light exposure, by means of the temperature-controlled fluid.

The device according to the invention enables opto-genetic effects, which can be induced by irradiation of living cells with light, to be measured reversibly and in real time by means of the flow cytometer. The potential applications are many and varied and are also extended by a growing number of different dye indicators that can be applied to living cells.

BRIEF DESCRIPTION OF THE DRAWINGS

The invention will be described below without restriction of the general scope of the invention, with the aid of exemplary embodiments and with reference to the drawings. Shown are.

MEANS OF EMBODYING THE INVENTION, INDUSTRIAL APPLICABILITY

Figure 1A:
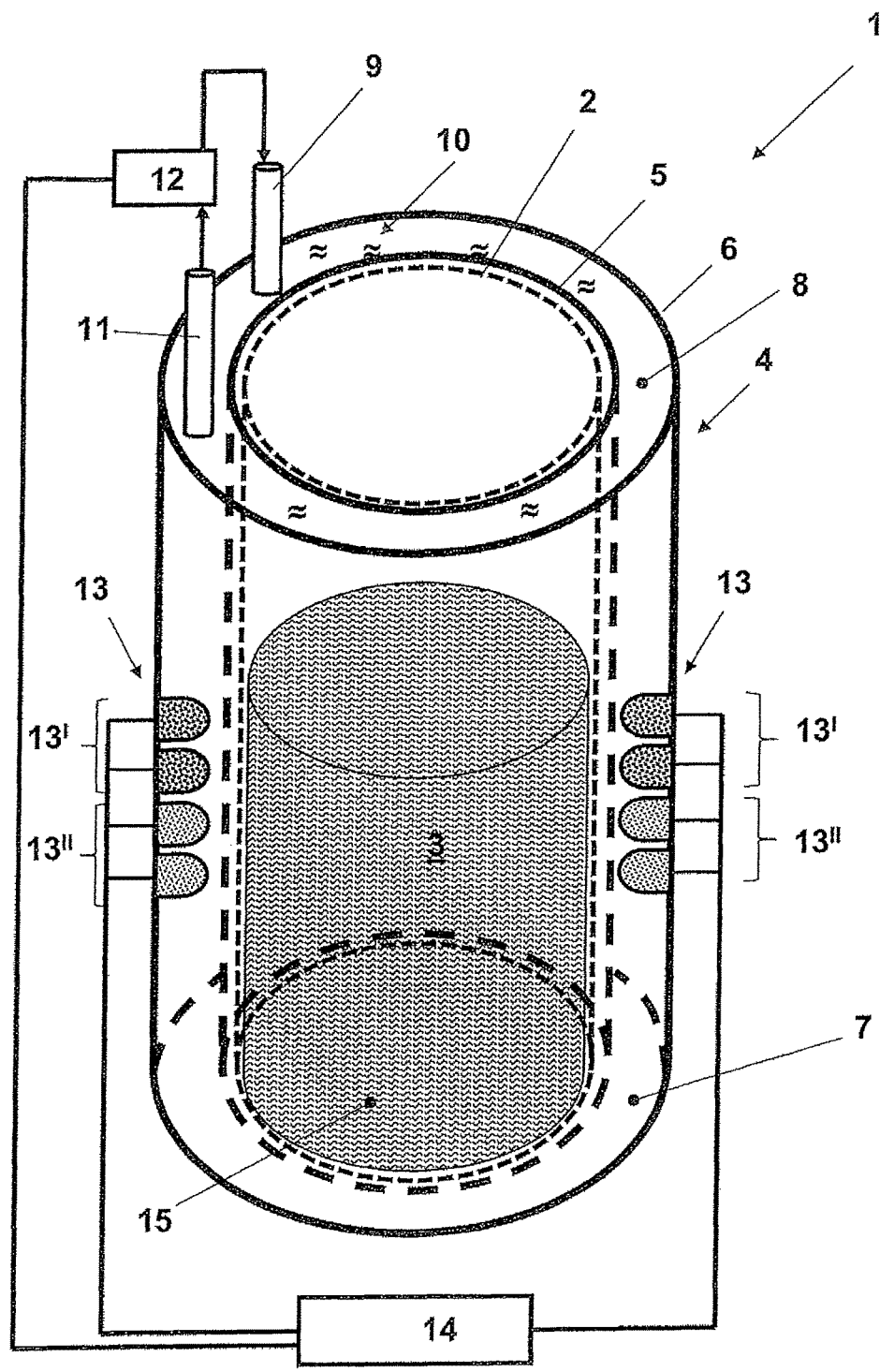
FIGS. 1a, b illustrate respectively a schematic view and a cross section view of a preferred exemplary embodiment for the optical stimulation of a biological sample with a controlled quantity of light and under a controlled temperature level.

FIG. 1a shows a schematic view of a preferred exemplary embodiment for implementing a device 1 for the optical stimulation of an optically activatable biological sample 3 located in a sample container 2. The device has a container 4, implemented in the form of a straight hollow cylinder, whose inner peripheral surface 5, outer peripheral surface 6 and annular base plate 7 bound a flow volume 8 open at the top. The flow volume 8 therefore represents an annular, cup-like volume, into which via a supply pipe 9 a fluid 10, preferably water, is introduced, which preferably completely fills the flow volume 8. The fluid 10 is fed via an outlet line 11 of a temperature control unit 12, which by operation of the pump sets the fluid into a constant fluid circulation, so that the fluid located in the flow volume 8 always has a homogeneous temperature that can be specified using the temperature control unit 12.

Within the flow volume 8 a plurality of LED light sources 13 is arranged, which come directly into contact with the temperature-controlled fluid 10. The plurality of the light sources 13 at least partly protruding into the flow volume 8 can be divided into at least two different light source groups 13' and 13", which differ from each other in terms of their different emission characteristics, such as wavelength and intensity. The LED light sources 13, and also the temperature control unit 12, are connected to a control and/or regulation unit 14, which ensures both a constant selectable temperature level of the fluid inside the flow volume 8 as well as a constant emission of the individual light sources 13. The inner peripheral surface 5 is optically transparent, that is, it is designed preferably fully transparent, at least for the wavelengths emitted by the LED light sources 13. The inner peripheral surface 5 also constitutes a bounding wall, which together with a lower base plate 15, which also forms the lower bounding wall of the cup-shaped container 4, bounds a cylindrically designed receiving volume open on one side, into which the cuvette-like sample container 2 can be inserted from above, which is at least partly filled with the optically activatable biological sample 3. The outer peripheral surface 6, on the other hand, is non-transparent, so that no light at all can enter the external environment. This is advisable for safety-relevant reasons, especially in cases where UV light-emitting light sources are used.

The sample container 2 and the bounding wall and/or inner peripheral surface 5 of the container 4 comprising the flow volume 8 are matched with regard to their size and spatial form in such a way that the sample container 2, and thus the suspended biological sample 3 located therein, is thermally coupled to the temperature-controlled liquid 10 via the bounding wall 5. In this way, both the LED light sources 13 and the biological sample located in the sample container 2 are held at a constant specifiable temperature level. The gap between the sample container 2 and the inner peripheral surface 5 is dimensioned in such a way that an easy insertion of the sample container 2 into the receiving volume and a corresponding removal are both possible, while at the same time ensuring the most intimate, i.e., loss-less, thermal coupling possible between the sample container 2 and the inner peripheral surface 5, or bounding wall.

Figure 1B:
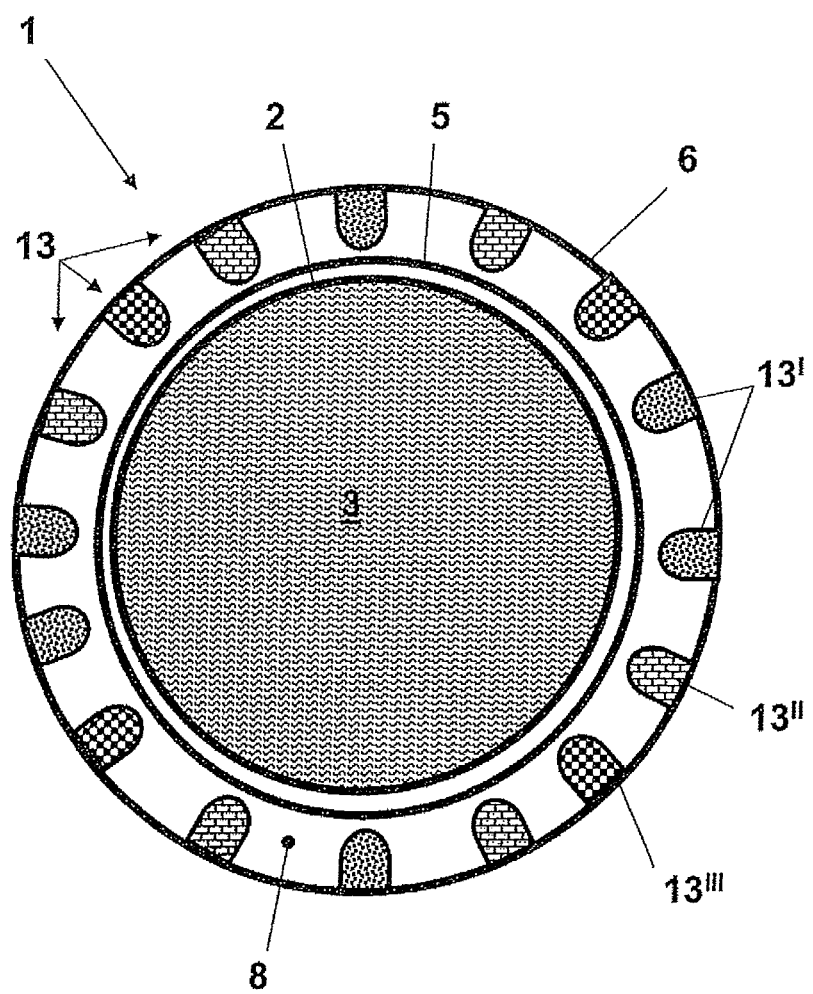

FIG. 1b shows a cross-sectional view through the device 1, from which the arrangement of a plurality of individual LED light sources 13, which are preferably evenly distributed in the circumferential direction around the hollow cylindrical device 1, is apparent. The different shadings of the individual LED light source 13 are intended to illustrate that LED light sources of different wavelength are also distributed in the circumferential direction U. Let it thus be assumed that the device illustrated in FIG. 1b is equipped with three different LED light sources 13', 13", 13'".

Figure 2:
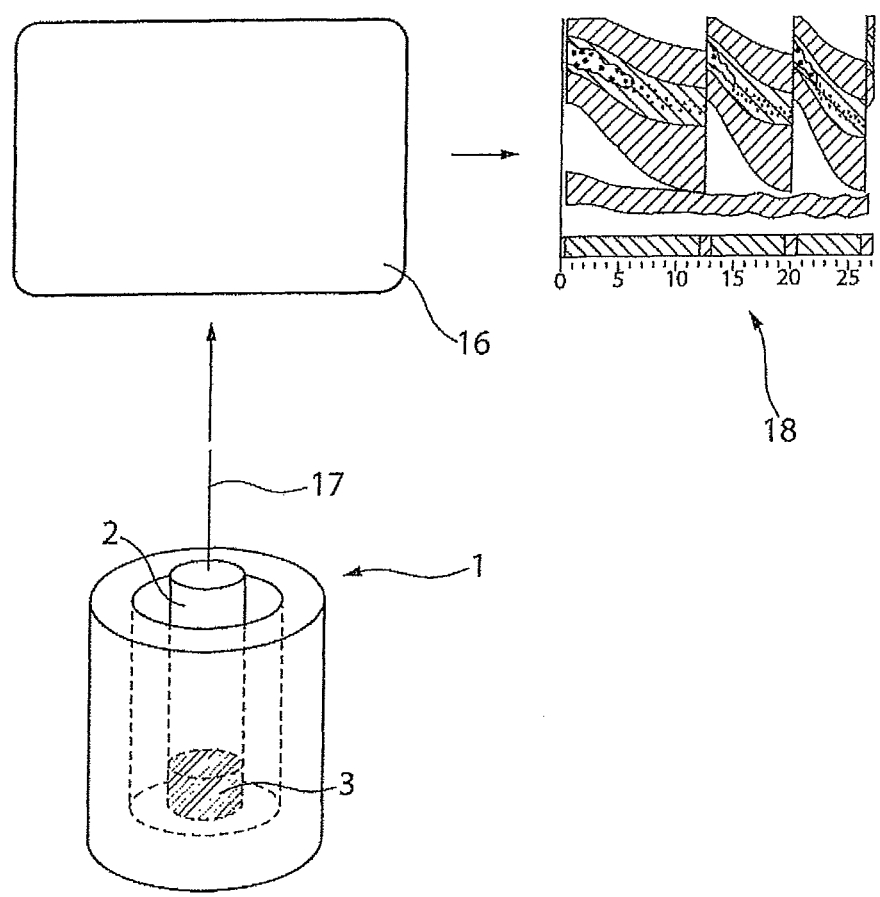
FIG. 2 illustrates arrangement for analysing an optically activated biological sample.

FIG. 2 shows a combination of the device 1 illustrated in FIG. 1a, b for optical stimulation of the optically activatable biological sample 3 positioned in the sample container 2 with a flow cytometer 16, the supply line or measuring capillary 17 of which protrudes into the sample container 2 from above to provide a suction of the sample into the flow cytometer 16. By means of this direct combination a cytometric measurement of the biological sample 3 is possible before, during and after the controlled execution of an optical stimulation. In this way, cytometric measurements can be carried out on living cells under controlled conditions, in order to obtain a cytometric measurement result 18, on the basis of which empirical information can be obtained about optically stimulated changes with regard to biological signals and signalling pathways in the cell. For more explanation, refer to FIG. 3b. The potential applications of the device according to the invention are numerous, and an example will be explained in more detail below.

The so-called Syk-kinase represents a central regulating kinase in B-lymphocytes as well as in many other cell types and forms the basis for a cyto-metric examination. Both end sections of the Syk-kinase are merged with one Dronpa protein each for the purpose of the optical activation. Dronpa proteins dimerise when irradiated with light of a wavelength of 400 nm and diffuse when irradiated with light of 500 nm.

Figure 3A:
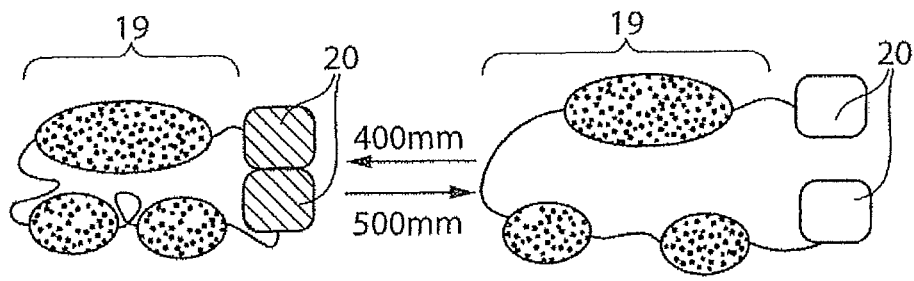
FIG. 3a illustrates the optically activatable process in accordance with the invention.

This optically activatable process is illustrated in FIG. 3a. It should be assumed that the enzyme Syk-kinase 19 is in each case merged with a Dronpa protein 20 on both sides, at the ends. By irradiation of the Dronpa-Syk-Dronpa merged protein 19+20, the conformation and thus the activity of the Syk-kinase can be regulated by light. By irradiation with light of a wavelength of 400 nm, the Dronpa dimerisation and a conformational change towards the closed, inactive form of Syk 19 is induced, which is illustrated in the left-hand image in FIG. 3b. If, on the other hand, the Dronpa-Syk-Dronpa merged protein 19+20 is irradiated with light of a wavelength of 500 nm, then a Dronpa dissociation and a conformational change to the open and an active form of Syk is induced as shown in the right-hand image of FIG. 3b.

Figure 3B:
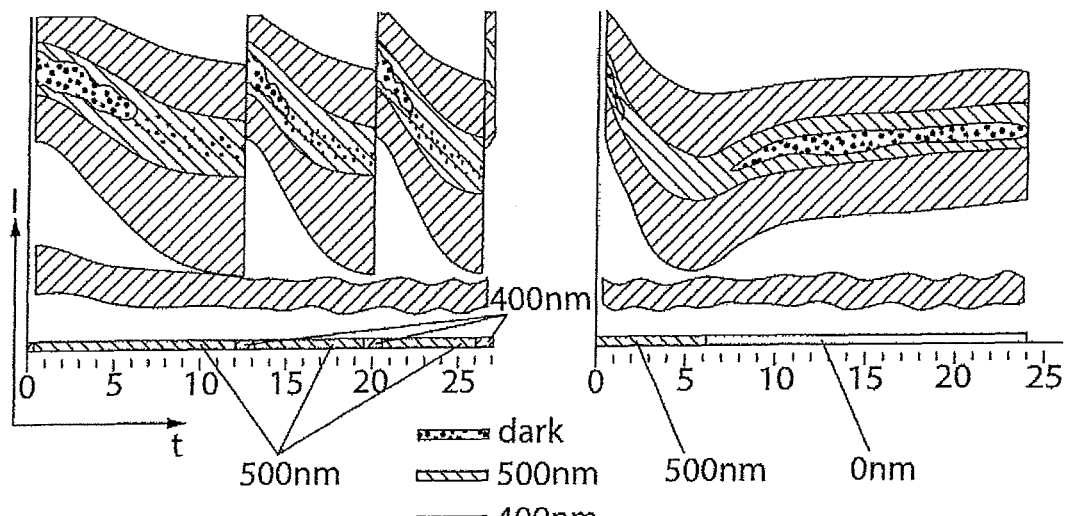
FIG. 3b illustrates an opto-genetic response of a biological sample using the example of the Syk-kinase.

In fact the dissociated Dronpa does not fluoresce, while only the dimerised form Dronpa fluoresces To verify whether the device according to the solution is able to dimerise, and also to de-dimerise the Dronpa-Syk-Dronpa merged protein 19+20, measurements as shown in FIG. 3b were carried out against time t in minutes. For the measurement and analysis, the property of the Dronpa is used that dissociated Dronpa does not fluoresce, while only the dimerised form of Dronpa fluoresces.

In the graphs illustrated in FIG. 3b, the fluorescence intensity I of the fluorescent dye GFP is shown along the Y-axis, which is used as an indicator of the association or dissociation of Dronpa. The lower coloured bar in each of the two diagrams in FIG. 3b indicates the wavelength at which the cell suspension was irradiated over the time t.

It is clearly apparent from the measurement results that under irradiation with green light, in other words with wavelengths of 500 nm, the Dronpa fluorescence intensity decreases significantly, which means Dronpa dissociates, as shown in FIG. 3a. On the other hand, under irradiation with violet light, in other words with a wavelength of 400 nm, the fluorescence intensity of Dronpa increases significantly, which means Dronpa dimerises.

Figure 3C:
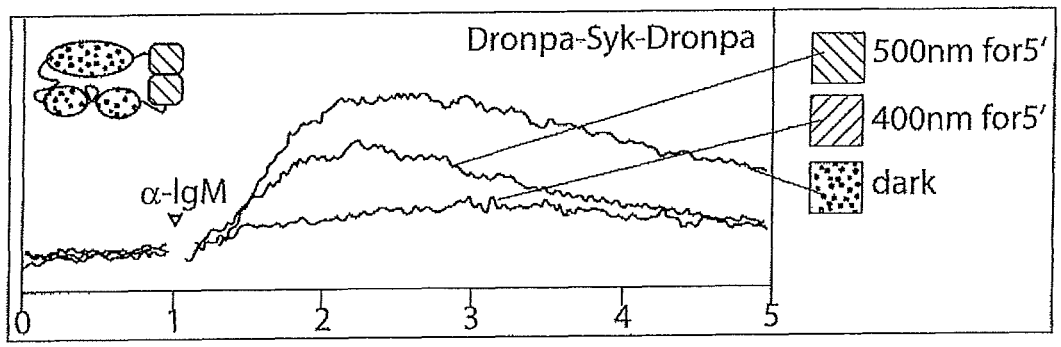
FIG. 3c illustrates a graphical representation of the measurement results obtained by use of a flow cytometer.

With the conditions given above, calcium measurements were subsequently carried out for the photo-regulation of Syk. To this end, the cells to be tested were initially combined with a calcium dye, with which the relative calcium influx can be measured. The cells coloured in this way are irradiated, or stimulated, within the device according to the solution with corresponding wavelengths. At the same time, optically activated cells are transferred from the sample container into the flow cytometer for analysis. In the graph of FIG. 3c the relative values of calcium influx into the cell are shown on the y-axis against time in minutes on the x-axis. The cells were either not illuminated during the entire measurement in accordance with the label (dark), or illuminated with 400 nm or 500 nm. At the same time, the cells are stimulated with anti-IgM (see arrow in the diagram) in order to initiate a calcium influx. The results plotted in FIG. 3c show that the calcium flux of the cells can be regulated by light-induced change in the conformation of the Dronpa-Syk-Dronpa merged protein.

In summary, it can be concluded that the device according to the solution is ideally suited to the analysis of opto-genetically regulated signal pathways in living cells. In the example shown above, the conformation of a kinase, and therefore its activity, were opto-genetically regulated.

The experimental possibilities of the use of the device according to the solution, however, extend far beyond the calcium measurement described above. Thus, in principle any dye indicator that can be applied to living cells can be optically activated using the device according to the solution in a controlled and reproducible way. The device according to the solution also offers the capability of stimulating cells with so-called "photo-cage components" and "photo-activatable reagents". This includes a plurality of substances that can be released or activated by irradiation with light of a specific wavelength.

An example of this is the so-called "DMNB-caged cAMP". The signalling molecule cAMP is released by irradiation with light of a wavelength of 350 nm. By means of the device according to the invention, effects of the released cAMP can be directly measured.

LIST OF REFERENCE NUMERALS 1 device for optical stimulation of a biological sample
2 sample container
3 biological sample
4 cup-like designed housing
5 inner peripheral surface
6 outer peripheral surface
7 annular base plate
8 flow volume 9 supply line
10 fluid
11 outlet line
12 temperature control unit
13 LED
13'-13V LED groups
14 control and/or regulation unit
15 base plate
16 flow cytometer
17 measuring capillary
18 measurement result
19 Syk-kinase
20 Dronpa

The invention claimed is:

1. A device for optical stimulation of an optically activatable biological sample with at least one light source, which emits light of at least one selectable wavelength, which impinges onto the sample, wherein: the at least one light source is thermally directly coupled to a section of a hollow channel; the section of the hollow channel is part of a fluid circuit through which fluid flows; a temperature control and a conveying pump is located along the fluid circuit; and the section of the hollow channel has at least one boundary wall onto which an optically activatable biological sample is thermally coupled thereto.

2. A device according to claim 1, wherein:
at least a part of the at least one light source is located inside the section of the hollow channel.

3. A device according to claim 2, wherein:
the section of the hollow channel comprises a hollow cylinder including an inner and outer peripheral surface bounding a volume of the fluid circuit in a radial direction; and
the inner peripheral surface represents at least one boundary wall and is transparent to the light of the at least one light source, and the at least one light source includes an emission aperture which is oriented radially inward.

4. A device according to claim 3 wherein:
a plurality of light sources are oriented in at least one of an axial and a circumferential direction of the section of the hollow channel.

5. A device according to claim 4, wherein:
the light sources are divided into at least two groups, each group containing at least one light source and differing from each other in one of radiation intensity, emitted wavelength or wavelength spectrum.

6. A device according claim 2, wherein:
the at least one light source is an LED or a laser-based light source.

7. A device according claim 2, wherein:
the optically activatable biological sample is stored in a sample container;
the sample container is an optically transparent, cuvette-like vessel which bounds a receiving volume; and
the at least one bounding wall of the section of the hollow channel is part of a receiver, into which the sample container can be inserted, so that the at least one bounding wall completely encloses the sample container in the circumferential direction thereof.

8. A device according to claim 1, wherein:
the section of the hollow channel comprises a hollow cylinder including an inner and outer peripheral surface bounding a volume of the fluid circuit in a radial direction; and
the inner peripheral surface represents at least one boundary wall and is transparent to the light of the at least one light source, and the at least one light source includes an emission aperture which is oriented radially inward.

9. A device according to claim 8 wherein:
a plurality of light sources are oriented in at least one of an axial and a circumferential direction of the section of the hollow channel.

10. A device according to claim 9, wherein:
the light sources are divided into at least two groups, each group containing at least one light source and differing from each other in one of radiation intensity, emitted wavelength or wavelength spectrum.

11. A device according claim 10, wherein:
the at least one light source is an LED or a laser-based light source.

12. A device according claim 10, wherein:
the optically activatable biological sample is stored in a sample container;
the sample container is an optically transparent, cuvette-like vessel which bounds a receiving volume; and
the at least one bounding wall of the section of the hollow channel is part of a receiver, into which the sample container can be inserted, so that the at least one bounding wall completely encloses the sample container in the circumferential direction thereof.

13. A device according claim 9, wherein:
the at least one light source is an LED or a laser-based light source.

14. A device according claim 9, wherein:
the optically activatable biological sample is stored in a sample container;
the sample container is an optically transparent, cuvette-like vessel which bounds a receiving volume; and
the at least one bounding wall of the section of the hollow channel is part of a receiver, into which the sample container can be inserted, so that the at least one bounding wall completely encloses the sample container in the circumferential direction thereof.

15. A device according claim 8, wherein:
the at least one light source is an LED or a laser-based light source.

16. A device according claim 8, wherein:
the optically activatable biological sample is stored in a sample container;
the sample container is an optically transparent, cuvette-like vessel which bounds a receiving volume; and
the at least one bounding wall of the section of the hollow channel is part of a receiver, into which the sample container can be inserted, so that the at least one bounding wall completely encloses the sample container in the circumferential direction thereof.

17. A device according claim 1, wherein:
the at least one light source is an LED or a laser-based light source.

18. A device according claim 17, wherein:
the optically activatable biological sample is stored in a sample container;
the sample container is an optically transparent, cuvette-like vessel which bounds a receiving volume; and
the at least one bounding wall of the section of the hollow channel is part of a receiver, into which the sample container can be inserted, so that the at least one bounding wall completely encloses the sample container in the circumferential direction thereof.

19. A device according claim 1, wherein:
the optically activatable biological sample is stored in a sample container;

the sample container is an optically transparent, cuvette-like vessel which bounds a receiving volume; and the at least one bounding wall of the section of the hollow channel is part of a receiver, into which the sample container can be inserted, so that the at least one bounding wall completely encloses the sample container in the circumferential direction thereof.

20. A device according to claim 19, wherein:

dimensions of the receiver and the sample container are matched so that the sample container when inserted condition inside the receiver structure is adjacent to the boundary wall and is thermally coupled thereto.

21. A device according to claim 1, wherein the boundary wall is proximate to a receiving volume for at least partial filling the receiving volume with a suspension of an optically activatable biological sample.

22. A device according to claim 1, comprising:

at least one of a control and regulator for controlling or regulating the temperature control, the fluid pump and the at least one light source in accordance with a selectable irradiation time of the sample with light of a constant selectable light intensity and wavelength of a selectable wavelength spectrum at a controlled temperature within the fluid circuit through which the fluid flows.

23. An arrangement for examining an optically activated biological sample, having a device according to claim 22 and a flow cytometer, which is in fluidic connection with a receiving volume via a connecting line.

24. An arrangement according to claim 23, wherein:

at least one of the control and regulator transfers signals by wire or wirelessly to and from a control of the flow cytometer to provide pump-based extraction of at least a portion of the sample from the receiver volume via the fluidic connection to the flow cytometer for initiation of a subsequent examination of the sample.

25. A use of the arrangement according to claim 24, comprising performing examination of at least one optically regulated signaling pathways and signaling molecules in biological cells.

26. A method for carrying out a cytometric examination of an optically activated biological sample, for a controlled optical activation of light with a controlled and selectable light intensity with at least one of a selected wavelength and a selected wavelength spectrum which irradiates the sample, wherein the light is emitted by at least one light source, which is temperature-controlled by a temperature-controlled fluid, to which the sample is thermally directly coupled during irradiation with the light sample.

27. A method according to claim 26, wherein before and at least one of during and after the light irradiation of the biological sample, the sample is temperature controlled by the temperature-controlled fluid.

28. A method according to claim 26, wherein the temperature-controlled liquid flows through a hollow channel section, to which both the biological sample and the at least one light source are thermally coupled and the biological sample and the at least one light source are temperature-controlled by convection from the temperature controlled liquid.

* * * * *